(12) United States Patent
Dorn (10) Patent No.: US 8,790,385 B2
(45) Date of Patent: Jul. 29, 2014

(54) STRAIN MANAGEMENT IN STENT DELIVERY SYSTEM

(75) Inventor: Jurgen Dorn, Neulussheim (DE)

(73) Assignee: C. R. Bard, Inc., Murray Hill, NJ (US)

( * ) Notice: Subject to any disclaimer, the term of this patent is extended or adjusted under 35 U.S.C. 154(b) by 2147 days.

(21) Appl. No.: 10/555,228

(22) PCT Filed: May 10, 2004

(86) PCT No.: PCT/EP2004/004974
§ 371 (c)(1),
(2), (4) Date: Oct. 31, 2005

(87) PCT Pub. No.: WO2004/098692
PCT Pub. Date: Nov. 18, 2004

(65) Prior Publication Data
US 2007/0055338 A1 Mar. 8, 2007

(30) Foreign Application Priority Data

May 9, 2003 (GB) .................................. 0310714.1

(51) Int. Cl.
*A61F 2/06* (2013.01)
(52) U.S. Cl.
USPC ...................................................... 623/1.11
(58) Field of Classification Search
USPC .......... 623/1.12, 1.11, 1.2; 606/108; 600/585; 604/526
See application file for complete search history.

(56) References Cited

U.S. PATENT DOCUMENTS

| | | | |
|---|---|---|---|
| 4,795,458 A * | 1/1989 | Regan | 623/1.19 |
| 4,898,591 A | 2/1990 | Jang et al. | |
| 4,917,666 A * | 4/1990 | Solar et al. | 604/95.01 |
| 4,950,227 A * | 8/1990 | Savin et al. | 623/1.12 |
| 5,376,083 A * | 12/1994 | Mische | 604/264 |

(Continued)

FOREIGN PATENT DOCUMENTS

| | | |
|---|---|---|
| EP | 1181906 | 2/2002 |
| EP | 0836447 | 12/2002 |

(Continued)

OTHER PUBLICATIONS

Office Action from U.S. Appl. No. 10/554,964, mailed Feb. 6, 2007.

(Continued)

*Primary Examiner* — Thomas McEvoy
(74) *Attorney, Agent, or Firm* — Rutan & Tucker, LLP (57) ABSTRACT

A percutaneous, transluminal system with a distal end for inserting into a body and a proximal end to remain outside the body, and comprising: an inner catheter which runs the length of the system and has a distal end and a proximal end, the inner catheter itself comprising: an inner tube (102); a wire coil (110) disposed around at least a portion of the inner tube, having a distal end, a proximal end, a distal region (114), an intermediate region and a proximal region (112); and an outer tube (124), having a distal end and a proximal end, disposed around at least a portion of the wire coil reinforcing member, characterized by: the wire coil having a closed-coil structure in the intermediate region and an open-coil structure in at least one of the distal region and the proximal region; and by a flow path for liquid from the proximal to the distal end of the system which includes a radially-extending portion through said open coil structure.

14 Claims, 3 Drawing Sheets

(56) References Cited

U.S. PATENT DOCUMENTS

| | | | |
|---|---|---|---|
| 5,415,664 A * | 5/1995 | Pinchuk | 623/1.11 |
| 5,417,708 A * | 5/1995 | Hall et al. | 606/200 |
| 5,445,646 A | 8/1995 | Euteneuer et al. | |
| 5,458,615 A | 10/1995 | Klemm et al. | |
| 5,571,135 A | 11/1996 | Fraser et al. | |
| 5,603,705 A | 2/1997 | Berg | |
| 5,643,278 A | 7/1997 | Wijay | |
| 5,674,208 A | 10/1997 | Berg et al. | |
| 5,676,696 A | 10/1997 | Marcade | |
| 5,690,643 A | 11/1997 | Wijay | |
| 5,695,499 A | 12/1997 | Helgerson et al. | |
| 5,733,267 A | 3/1998 | Del Toro | |
| 5,772,669 A | 6/1998 | Vrba | |
| 5,788,707 A | 8/1998 | Del Toro et al. | |
| 5,951,495 A | 9/1999 | Berg et al. | |
| 5,954,651 A | 9/1999 | Berg et al. | |
| 5,957,930 A | 9/1999 | Vrba | |
| 5,997,487 A | 12/1999 | Kolehmainen et al. | |
| 6,019,778 A | 2/2000 | Wilson et al. | |
| 6,042,578 A | 3/2000 | Dinh et al. | |
| 6,212,422 B1 | 4/2001 | Berg et al. | |
| 6,217,595 B1 | 4/2001 | Shturman et al. | |
| 6,238,402 B1 | 5/2001 | Sullivan, III et al. | |
| 6,254,611 B1 | 7/2001 | Vrba | |
| 6,342,066 B1 | 1/2002 | Toro et al. | |
| 6,368,344 B1 * | 4/2002 | Fitz | 623/1.11 |
| 6,391,051 B2 | 5/2002 | Sullivan, III et al. | |
| 6,425,898 B1 | 7/2002 | Wilson et al. | |
| 6,505,066 B2 | 1/2003 | Berg et al. | |
| 6,514,261 B1 * | 2/2003 | Randall et al. | 606/108 |
| 6,530,947 B1 | 3/2003 | Euteneuer et al. | |
| 6,533,807 B2 * | 3/2003 | Wolinsky et al. | 623/1.15 |
| 6,579,305 B1 * | 6/2003 | Lashinski | 623/1.11 |
| 6,660,031 B2 | 12/2003 | Tran et al. | |
| 6,676,666 B2 | 1/2004 | Vrba et al. | |
| 6,695,862 B2 * | 2/2004 | Cox et al. | 606/191 |
| 6,702,802 B1 | 3/2004 | Hancock et al. | |
| 6,726,712 B1 | 4/2004 | Raeder-Devens et al. | |
| 6,736,839 B2 | 5/2004 | Cummings | |
| 6,773,446 B1 * | 8/2004 | Dwyer et al. | 606/191 |
| 6,884,257 B1 * | 4/2005 | Cox | 623/1.11 |
| 7,001,423 B2 | 2/2006 | Euteneuer et al. | |
| 7,105,014 B2 | 9/2006 | Murray, III | |
| 7,331,985 B2 * | 2/2008 | Thompson et al. | 623/1.11 |
| 2001/0016726 A1 * | 8/2001 | Dubrul et al. | 604/509 |
| 2002/0016597 A1 | 2/2002 | Dwyer et al. | |
| 2002/0045929 A1 | 4/2002 | Diaz | |
| 2003/0050686 A1 | 3/2003 | Raeder-Devens et al. | |
| 2003/0083623 A1 | 5/2003 | Berg et al. | |
| 2003/0135266 A1 * | 7/2003 | Chew et al. | 623/1.16 |
| 2003/0171770 A1 * | 9/2003 | Kusleika et al. | 606/200 |
| 2004/0102791 A1 * | 5/2004 | Murray, III | 606/108 |
| 2004/0148000 A1 * | 7/2004 | Bilge | 623/1.11 |
| 2004/0215317 A1 | 10/2004 | Cummings | |
| 2005/0027345 A1 * | 2/2005 | Horan et al. | 623/1.12 |
| 2005/0165352 A1 | 7/2005 | Henry et al. | |
| 2005/0209674 A1 * | 9/2005 | Kutscher et al. | 623/1.11 |

FOREIGN PATENT DOCUMENTS

| | | |
|---|---|---|
| EP | 1622669 A1 | 2/2006 |
| JP | 09-84880 A | 5/1976 |
| JP | 02-501712 T | 6/1990 |
| JP | 02-172474 | 7/1990 |
| JP | 03-501712 | 4/1991 |
| JP | 06-023057 | 2/1994 |
| JP | 2002-102357 A | 4/2002 |
| JP | 2002-515769 A | 5/2002 |
| JP | 2002-527119 A | 8/2002 |
| JP | 2006-525835 A | 11/2006 |
| MX | PA05012012 A | 2/2006 |
| WO | 8903250 A1 | 4/1989 |
| WO | WO96/13228 | 5/1996 |
| WO | 0147436 A2 | 7/2001 |
| WO | 0154614 A2 | 8/2001 |
| WO | WO01/34240 | 5/2002 |

OTHER PUBLICATIONS

Office Action from U.S. Appl. No. 10/554,964, mailed Aug. 15, 2007.
Office Action from U.S. Appl. No. 10/554,964, mailed Apr. 16, 2008.
CA 2525197 filed May 10, 2004 Notice of Allowance dated May 13, 2011.
CA 2525197 filed May 10, 2004 Office Action dated May 20, 2010.
EP 04731911 filed May 10, 2004 Notice of Grant dated Nov. 13, 2008.
EP 04731911 filed May 10, 2004 Office Action dated Jul. 13, 2007.
EP 04731911 filed May 10, 2004 Office Action dated May 31, 2007.
JP 2006-505408 filed May 10, 2004 Office Action dated Apr. 26, 2011.
JP 2006-505408 filed May 10, 2004 Office Action dated May 17, 2010.
PCT/EP2004/004974 filed May 10, 2004 International Preliminary Report on Patentability dated Nov. 11, 2005.
PCT/EP2004/004974 filed May 10, 2004 Search Report dated Nov. 2, 2004.
PCT/EP2004/004974 filed May 10, 2004 Written Opinion dated Nov. 2, 2004.
U.S. Appl. No. 10/554,964, filed Dec. 15, 2005 Advisory Action dated Oct. 23, 2007.
U.S. Appl. No. 10/554,964, filed Dec. 15, 2005 Final Office Action dated Mar. 13, 2009.

* cited by examiner

Fig. 2

Fig. 3

STRAIN MANAGEMENT IN STENT DELIVERY SYSTEM

PRIORITY

This application is a national stage application under 35 USC §371 of International Application No. PCT/EP2004/004974, filed May 10, 2004, claiming priority to United Kingdom Application No. GB 0310714.1, filed May 9, 2003, each of which is incorporated by reference into this application as if fully set forth herein.

BACKGROUND OF THE INVENTION

This invention relates to medical devices and, more particularly, but not exclusively, to devices for performing minimally-invasive surgical procedures.

When performing medical operations, it is of paramount importance that the surgery itself causes as little trauma to the patient as possible. For this reason, medical science is continually developing new and improved methods for treating patients and reducing the risk of severe consequences arising from the procedure itself. In recent years, techniques such as keyhole surgery and endoluminal or transluminal treatments, which avoid the need for traumatic open surgery, have become common practice in many parts of the world. Benefits to the patient include reduced external scarring, minimal trauma during surgery, reduced risk of infection and shorter recovery periods. Correspondingly, there has been a demand for new and improved surgical equipment, capable of performing minimally invasively the functions required to successfully treat the numerous and varying medical conditions. As a result, there is ever-increasing pressure for individual instruments to combine an increasing range of functions, to be of smaller dimensions and to maintain or improve the accuracy and manipulability of the devices.

In the specific field of transluminal or endoluminal surgery, one drive is towards reducing the diameter of devices to be inserted into and guided along a body lumen, in order to allow surgical procedures to be performed in narrow conduits such as blood vessels which are inaccessible to larger devices. At the same time, it is necessary to ensure that the devices can perform to a high level of accuracy and can be easily directed and controlled by the surgeon, particularly when they have to be guided through the tortuous passageways such as are defined by inter-connecting blood vessels within the human body.

Common procedures include the treatment of coronary diseases and deficiencies by the endoluminal implantation and deployment of stents or replacement valve structures at locations where the natural blood vessels have become defective, blocked or damaged. In such a procedure, a medical device is loaded onto or into a delivery catheter in a compressed or reduced-diameter configuration. The catheter is then inserted through an incision into a blood vessel, typically the femoral artery, and guided through the passageway of inter-connecting blood vessels to the site requiring treatment. The medical device then expands or is expanded within the passageway at the treatment site, where it remains. The delivery catheter is then retracted through the passageway and removed through the same incision.

EP-A-0 836 447 discloses a stent delivery system comprising an inner core, having a proximal end and a distal end, made from a wire coil; a stent concentrically arranged around the inner coil near the distal end; a sheath concentrically arranged around the inner coil extending from the proximal end to a distal end proximal of the stent; an outer sheath covering the stent; and means for retracting the outer sheath. When the delivery system has been inserted and guided to the correct location, the outer sheath is retracted, releasing the stent contained therein. During insertion of the catheter, the wire coil is flexible, allowing it to advance through the tortuous passageway defined by the inter-connecting blood vessels. During retraction of the outer sheath, the wire coil provides sufficient rigidity and resistance to axial compression to allow retraction of the outer sheath.

EP-A-1 181 906 discloses a similar stent delivery catheter, including a wire coil and further including a covering that fits over the coil to help resist buckling in bending and compression.

There is associated with endoluminal surgical procedures the need to visualize the position of the catheter as it is advanced through the bodily lumen, and to ensure that the device is properly located prior to, during and after deployment. In order to visualize the position of the advanced distal end of the catheter, pulses of visualizing fluid are injected into the bodily lumen so that the catheter distal end can be seen using visualisation means, such as radioscopy or fluoroscopy. In order to transport the visualizing fluid, prior art devices either provide a separate lumen within the catheter, for transporting visualizing fluid from the proximal end to the distal end of the catheter, or visualizing fluid may be injected through a guide catheter, within which the delivery catheter is advanced. In the latter system, the catheter can be provided with a shaft that is narrow except at the distal end, where the medical device is held, so that a sufficient volume of visualizing fluid can flow within the guide catheter lumen around the shaft and is not restricted until it reaches the distal end. A continuing preoccupation for catheter designs is how to provide sufficient quantity of visualizing fluid from a proximal end to a distal end of the delivery catheter without requiring an increased-diameter catheter and without restricting the flow past the delivery catheter.

With the prior art devices, there is often a trade-off between the flexibility of the delivery catheter and the resistance of the delivery catheter to compressive forces during retraction of the sheath containing the medical device. One method of mitigating this difficulty has been to reduce the length of the sheath relative to that of the medical device, and thereby reduce the friction force resisting retraction of the sheath during deployment of the medical device. A pull wire within the catheter can be used for controlled retraction of the sheath once the catheter is correctly positioned. In some prior art devices, the outer sheath is braided or has wire reinforcement to prevent the sheath from lengthwise stretching, so that the sheath will retract when the actuating means is operated and not just become longitudinally stretched. This results in the sheath having increased thickness. Therefore, another problem is to provide a system with reduced overall diameter that is flexible and controllable, without losing compression-resistance in the inner coil, and without the sheath stretching during retraction and incorrectly deploying or failing to deploy the medical device.

BRIEF SUMMARY OF THE INVENTION

In accordance with one aspect of the invention there is provided a percutaneous, transluminal system with a distal end for inserting into a body and a proximal end to remain outside the body, and comprising:
  an inner tube which runs the length of the system and has a distal end and a proximal end;

a wire coil disposed around at least a portion of the inner tube, having a distal end, a proximal end, a distal region, an intermediate region and a proximal region; and an outer tube, having a distal end and a proximal end, disposed around at least a portion of the wire coil, characterized by:

the wire coil having a closed-coil structure in the intermediate region and an open-coil structure in at least one of the distal region and the proximal region; and by a flow path for liquid from the proximal to the distal end of the system which includes a radially-extending portion through said open-coil structure.

According to another aspect of the present invention there is provided a system for a medical apparatus comprising:

a tube member having a distal end and a proximal end; and a sheath, having a distal end and a proximal end, disposed around at least a portion of the inner tube, said sheath being retractable in a proximal direction relative to the tube to perform an actuating step at the distal end of the system, by the application of an endwise tensile stress to the proximal end of the sheath, characterized in that:

the tube member resists the associated radially-inward contraction of the sheath which arises from the applied tensile stress during said actuating step.

According to various embodiments of medical surgical devices, there may be provided any, some or all of the following features either independently or in combination and according to any possible arrangement.

The inner tube can be made of any suitable material, such as a metal or polymeric material, having a distal end and a proximal end. The inner tube may define a lumen therethrough, which may be a lumen suitable for the insertion and retraction of a guide-wire. The inner tube is highly flexible and capable of navigating the tortuous channels such as in the biliary tree, arterial or venous system within the human body, and also provides some resistance to compression.

The wire coil, preferably a reinforcing coil, is made from a biologically compatible material, preferably a metal such as nickel-titanium alloy or stainless steel. The coil is disposed around the inner tube and provides torsional, radial and compressive reinforcement for that tube. At least one, and preferably both, of a proximal region and a distal region of the wire coil has an open-coil structure, whilst an intermediate region of the wire coil has a closed-coil structure. The wire coil is flexible and able to navigate the above-mentioned tortuous passageways defined by inter-connecting blood vessels. The wire coil is elastically extendable and compressible, but will remain substantially uncompressed under the attendant compressive forces normally encountered by such a member during the routine operational procedures required to operate the medical surgical device.

The outer tube is disposed about at least a portion of the inner tube. Preferably, the outer tube is a shrink-tube layer constraining the wire coil. The outer tube can be of any suitable material, and is preferably made from low friction PTFE. The outer tube is flexible and able to navigate tortuous bodily lumens. The outer tube gives added stability, and therefore compressive strength, to the wire coil, and prevents kinking of said coil during advancement through a tortuous passageway.

The wire coil in combination with the inner and outer tubes can define a fluid flow path between the inner and outer tubes and along a helical path defined by the adjacent turns of the wire coil. The fluid flow path may alternatively comprise a helical or an annular path between the coil and the outer tube, or between the coil and the inner tube, for example when the coil structure is such that substantially no fluid can pass from inside the coil to outside the coil or from outside the coil to inside the coil between the adjacent turns of the closed-coil structure.

There may be provided an outer sheath disposed around the outer tube, that advantageously has little or even no radial gap between the sheath and the outer tube. The outer sheath is made from any suitable polymeric material, and is preferably made from a thermoplastic elastomer such as the one sold by Du Pont under the trademark HYTREL. Although there is preferably minimal gap between the sheath and the outer tube, there may be provided a layer of lubricious material between the two, which may be a silicone coating on the outer surface of the outer tube. The sheath may even be in a circumferentially pre-stressed condition if the outside diameter of the outer tube is selected to be greater than the unstressed inner diameter of the sheath.

In a medical surgical device comprising an inner tube, wire coil, outer tube and sheath, the inner tube and sheath preferably extend from a proximal end to a point distal of the distal ends of the wire coil and outer tube. There may be provided at the end of the medical surgical device a tip. The tip may be formed as an atraumatic, tapered extension of the distal end of the sheath or the tip may be provided at the distal end of the inner tube, optionally as a separate element attached to the inner tube. Such an attached tip may be made from any suitable soft material such as a polyurethane like Pellethane (a registered trademark of Dow Chemical). The tip may be secured to the inner tube with a suitable adhesive, such as those sold by DYMAX Corporation.

In one preferred embodiment, the wire coil extends proximally of the outer tube by about 10 mm and extends distally of the outer tube by about 10 mm, with the proximal region and distal region of the wire coil being within (or comprising) the portions of the coil length extending beyond the outer tube and just inside it, whilst the intermediate region is the remaining, closed-coil, main part of the length of the wire coil lying within the lumen of the outer tube.

There may be provided near the distal end of the medical surgical device a pusher element disposed around the inner tube and adjacent the distal end of the wire coil. The pusher element can be attached to the wire coil distal end, for example by glueing with DYMAX glue. Attachment is achieved preferably without glue. One way to do this is to have an end region of the coil overlap radially outwardly over a proximally-extending annulus of the pusher and butting up against a proximal-facing shoulder of the pusher element.

The pusher element is advantageously made from PEEK. The pusher element may comprise a relatively long, cylindrical, proximal portion and a shorter, distal shoulder portion of larger diameter, with opposed shoulder surfaces facing proximally and distally. The pusher element is suitable for receiving on the distal-facing shoulder surface a proximal end face of an annular medical device such as a stent or stent graft, the proximal end of the medical device abutting the pusher element.

There may be provided a medical device at or near a distal end of the medical surgical apparatus. The medical device may be a self-expanding stent. The medical device can be disposed about a distal region of the inner tube which extends distally beyond the distal ends of the wire coil and outer tube. The medical device is accommodated proximal of any tip at the distal end of the medical surgical device and distal of any pusher element at the distal end of the wire coil. The medical device may be held in position by a sheath extending over at least a portion of, and preferably the entire length of, the medical device. A medical device which is a self-expanding stent or stent graft can be held within the sheath in a first, compressed state, to be released by retraction of the sheath in a proximal direction relative to the inner tube, wire coil and outer tube, the medical device being prevented from moving proximally by endwise compressive stress within the wire coil and any pusher element. When released, the medical device can expand, or be expanded, to a second, non-compressed state.

There may be provided at the distal end of the sheath a radiopaque marker and there may be provided at the distal end of the wire coil a radiopaque marker, such that release of the medical device is indicated by a movement of the radiopaque marker on the sheath to a position aligned with the radiopaque marker at the distal end of the wire coil, which indication can be viewed using visualizing means such as radioscopy or fluoroscopy. The radiopaque markers also serve to indicate the correct positioning of the medical device within a blood vessel or other body lumen during insertion and advancement of the medical surgical apparatus.

There may be provided at the proximal end of the medical surgical device actuating means connected, directly or indirectly, to the proximal ends of any inner tube, wire coil, outer tube or sheath. The actuating means is capable of holding the inner tube, wire coil and outer tube in place, and retracting the sheath in a proximal direction relative to the inner tube, wire coil and outer tube. The actuating means may be connected to the individual members directly, using means such as gluing, welding, etc. The inner tube and wire coil may be glued to a portion of the actuating means proximal of the portion of the actuating means to which the sheath is glued. Depending on the polymer present, the glue may be DYMAX glue.

The actuating means may include a Luer connection that communicates with the inner tube, wire coil and outer tube, the Luer providing access to an internal lumen of the inner tube.

The sheath may be connected to a second Luer providing access to a fluid flow path between the inner tube, outer tube and adjacent turns of the wire coil.

The actuating means may further include a Tuohy Borst valve, preventing fluid escaping from the proximal end of the medical surgical device. The actuating means may further comprise a swivel nut to lock the position of the sheath relative to the outer tube during insertion.

The actuating means may also provide a safety clip to prevent accidental retraction of the sheath during deployment.

In a medical surgical device comprising a wire coil between two tubular members, and where the wire coil has an open-coil structure at a proximal region and a distal region and a closed-coil structure in an intermediate region between the distal region and proximal region, a phenomenon is created whereby it is possible to introduce fluid into and through the gaps between the turns of the coil at a proximal region and then with a pressure differential urge said fluid along a fluid flow path defined between the adjacent turns of the coil and bounded outside and inside by the outer tube and the inner tube respectively. In this way, it is possible to advance the fluid along the helical path between the turns of the coil, even in the closed-coil structure of the intermediate section. In the case where the outer tube is tight on the outer cylindrical surface of the coil, but the inner tube is less tight on the luminal cylindrical surface of the coil, fluid can flow within an annular gap between the inner tube and the turns of the coil. The open-coil structure at the distal end of the coil allows an increased volume flow of fluid to exit radially outwardly at the distal end and increases the overall flow rate. In this way, no separate lumen is required for transferring the fluid, which may be a flushing fluid or visualizing fluid, and therefore results in a reduced overall diameter of the device. Because the main supporting member is the wire coil, the device remains highly flexible for advancement through tortuous passageways, yet is resistant to compressive forces associated with the retraction of an outer sheath. Therefore, the device can be advanced through narrower blood vessels whilst maintaining the required levels of controllability and ensuring accurate deployment of any medical devices to be delivered.

In one embodiment, an outer catheter sheath is disposed about the tube member, and the sheath extends along substantially the entire length of and distal of the tube member to enclose a compressed medical device, with the proximal end of the medical device abutting the distal end of the tube member, and the medical device having an equal or lesser diameter to the tube member when compressed. In this embodiment, no separate distal sheath is required. Because the proximal end of the medical device being inserted abuts the distal end of the inner tube member and both are covered by the outer sheath, no separate actuating member is required within the medical surgical device for proximal retraction of the sheath at the distal end, since this is achieved at a proximal end of the medical surgical device, resulting in a reduced-diameter delivery apparatus. Further, in this way, the diameter of the medical surgical device does not increase at the distal end where the medical device is located but remains constant along the entire length of the medical surgical device.

Alternatively, for delivery of medical devices having an irreducible diameter larger than what is needed for the shaft of the delivery system, the shaft may have a diameter substantially less than the distal end of the system where the medical device is housed. Where the polymeric sheath extends for substantially the entire length of the medical surgical device, and is disposed tightly around the tube member, and a tensile stress is applied to the outer sheath when the sheath is being retracted by actuating means at the proximal end, the outer sheath would normally tend to contract radially inwards, as the endwise tensile stress increases. In preferred embodiments of the invention, this tendency is inhibited, because the tube member located closely inside the outer sheath resists this radially inward motion. Hence, the two-dimensional stress matrix formed in the thin sheath is altered and results in the sheath behaving, effectively, less elastically. This means that the sheath will not stretch when the tensile force is applied, and allows for accurate deployment of the medical device contained therein. Further, the material of the outer sheath is observed to be capable of bearing an increased endwise tensile stress before it yields. The effect can be used to enable the sheath to be made without any reinforcing wire or braided structure or with reduced wall thickness and, consequently, of smaller outside diameter. This allows the designer to achieve a reduced overall diameter of the medical surgical device.

In a device as described above, it has been found that an inner tube member of PTFE, and an outer sheath of HYTREL with a lubricious material disposed between the two, possibly silicone, results in a very small coefficient of friction between the two layers. Indeed, these two materials behave almost as if they repel one another, which assists in retraction of the sheath for deployment of a medical device.

Further advantage is provided because of the ease of manufacture and assembly of the surgical medical apparatus. This is due to the ease with which the selected materials can be manufactured, and also due to the small number of component parts required to build such a device. This ought to reduce manufacturing time and costs.

It will be appreciated that the present invention is characterized by the support which the inner tube gives to the outer tube when the outer tube is in endwise tension when called upon to release from its distal end a medical implant such as a self-expanding stent. This support manifests itself in a smaller contraction of the diameter of the outer tube during release of the implant than would be the case in the absence of the inner tube. Accordingly, one way of discovering whether any particular co-axial delivery device utilises the teaching of the present disclosure is to examine the magnitude of diametrical contraction, with and without the presence of the inner tube. If the presence of the inner tube fails to reduce the amount of diametrical contraction, this would suggest that the support taught herein is not being given by the inner tube to the outer tube. In addition, the shape of the stress/elongation plot for the outer sheath is significantly different, depending whether the outer sheath is receiving support from the inner tube assembly

BRIEF DESCRIPTION OF THE DRAWINGS

Preferred embodiments of the invention will now be described, by way of example, and with reference to the accompanying drawings in which.

DETAILED DESCRIPTION OF THE PREFERRED EMBODIMENTS

Figure 1:
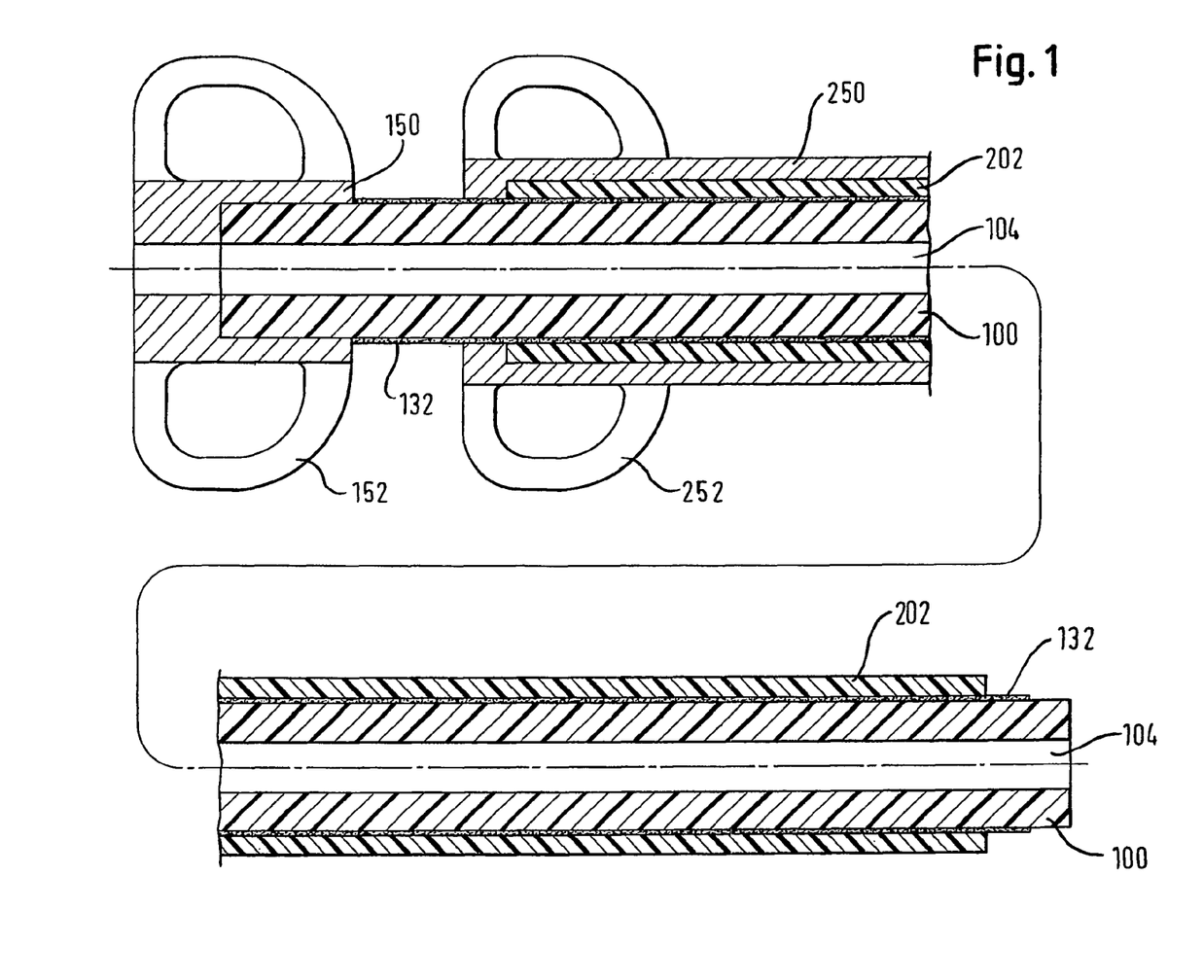
FIG. 1 is a longitudinal diametrical section through a stent delivery system according to a first embodiment of the invention.

FIG. 1 shows a system having a proximal end and a distal end. At the proximal end there is an actuating means 150, 152, 250, 252 connected to an elongate tube member 100 within the lumen of a sheath 202. There is a lubricious coating 132 applied to substantially the entire length of the tube member, which fills the annulus between the tube member and the sheath. The actuating means consists of a first connecting section 150 joined to the tube member 100 and having a pair of finger loops 152, and a second connecting means 250 attached to the sheath 202 having second manual gripping means also in the form of finger loops 252. The system has a central bore 104 therethrough, suitable for the insertion and retraction of a guide wire. The tube member 100 may be a single tube of polymeric material, or it may have a composite structure. The outside surface of the tube member is made from PTFE. The sheath is made from the thermoplastic elastomer HYTREL. The lubricious coating is a thin coating of silicone.

In operation, the actuating means is held in the open position, with connecting means 150 and 250 spaced apart, whilst the distal end of the system is inserted into and advanced along a body lumen. Once the distal end has reached the treatment site, the device is operated by retracting the actuator 250 proximally, which moves the actuating means to a closed position, with connecting means 150 and 250 adjacent one another. Closing the actuating means causes the sheath 202 to retract in a proximal direction relative to the tube member 100.

It is conceived that there may be located at the distal end of the system any one of a range of mechanisms operated by the retraction of said sheath, although the system is most immediately contemplated as for use as a catheter to deliver a stent or similar endoluminal medical surgical devices.

Because the sheath extends for substantially the entire length of the tube member, there will be a tensile force within the sheath during retraction, due to friction between the sheath and the distal device and the inner tube, and a resisting compressive force within the tube member. The gap between the tube member and sheath is sufficiently small to reduce radially inward contraction of the sheath under tensile stresses, thereby helping to prevent the sheath from stretching lengthwise. Further, the friction forces between the sheath and the tube member are kept small by judicious selection of the involved materials, which helps to prevent the compressive stress in the tube member from deforming it and displacing the distal tip proximally, which is particularly undesirable in an endoluminal device delivery system.

Figure 2:
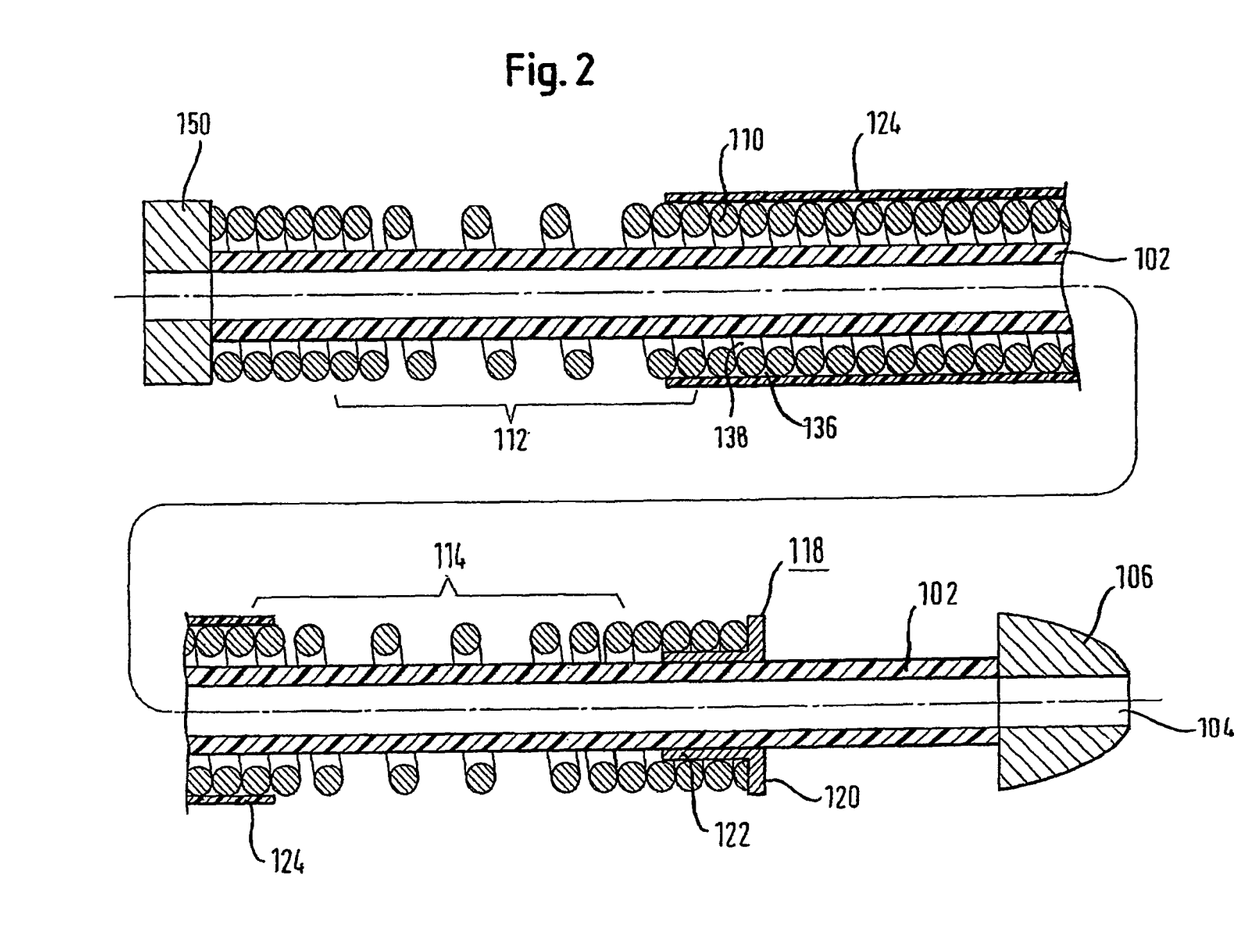
FIG. 2 is a longitudinal diametrical section through a stent delivery catheter according to a second embodiment of the invention.

FIG. 2 shows a cross-sectional view through a member forming part of a medical surgical apparatus. The member comprises a flexible inner tube 102, which is made from a polymeric material. At a distal end of the inner tube there is a tip 106, which is made from Pellethane. The inner tube and distal tip have an axial bore 104 running therethrough, which forms a guide wire lumen. Disposed around the inner tube, from the proximal end to a point near the distal end of the inner tube, is a wire coil 110. The wire coil is wound around the inner tube and has a distal region 114, a proximal region 112 and an intermediate region between the two. As illustrated, the wire coil has an open-coil structure in the distal region and proximal region, and a closed-coil structure throughout the intermediate region and in the short zones at the very proximal and distal ends of the coil. The wire-coil is made from stainless steel, providing the necessary flexibility and compression resistance.

At the distal end of the wire coil is a pusher element 118. The pusher element consists of a wider, proximal flange-like portion 120 and a narrower proximal shoulder portion 122 which receives radially about it the very distal end of the wire coil 110. The pusher element is made from PEEK, and is either attached to the wire coil using DYMAX glue or the distal end of the coil is tight enough around the cylinder 122 to need no glue. There is formed between the pusher element 118 and the distal tip 106 a region suitable for receiving a medical device for insertion into a body lumen. In particular, see FIG. 3, this medical device receiving area is capable of holding a self-expanding stent, with the distal end of the stent abutting the tip 106 and the proximal end of the stent disposed around a shoulder 123 of the pusher element and abutting the flange portion 120. The region may therefore be termed a "stent bed."

Disposed around the intermediate region of the wire coil 110 is an outer tube 124. This tube is a shrink-tube made of PTFE and fits tightly around the turns of the coil. The outer tube acts to constrain the wire coil in the desired shape and inhibits the coil from kinking during advancement of the member through a tortuous passageway, such as a body lumen. Because the outer tube is tight around the coil it inhibits the adjacent turns of the coil from overlapping one another. In this way, the wire coil structure provides good resistance to compressive forces occurring within the member. Prior to insertion of the member into a body lumen, flushing fluid can be passed through the fluid flow path defined between the inner tube, outer tube and adjacent turns of the wire coil. During a surgical procedure visualizing fluid may be transported from a proximal end of the member to a distal end of the member along the same fluid flow path. A gap between the coil and the inner tube 102 is the main fluid flow path in the intermediate region of the wire coil.

Figure 3:
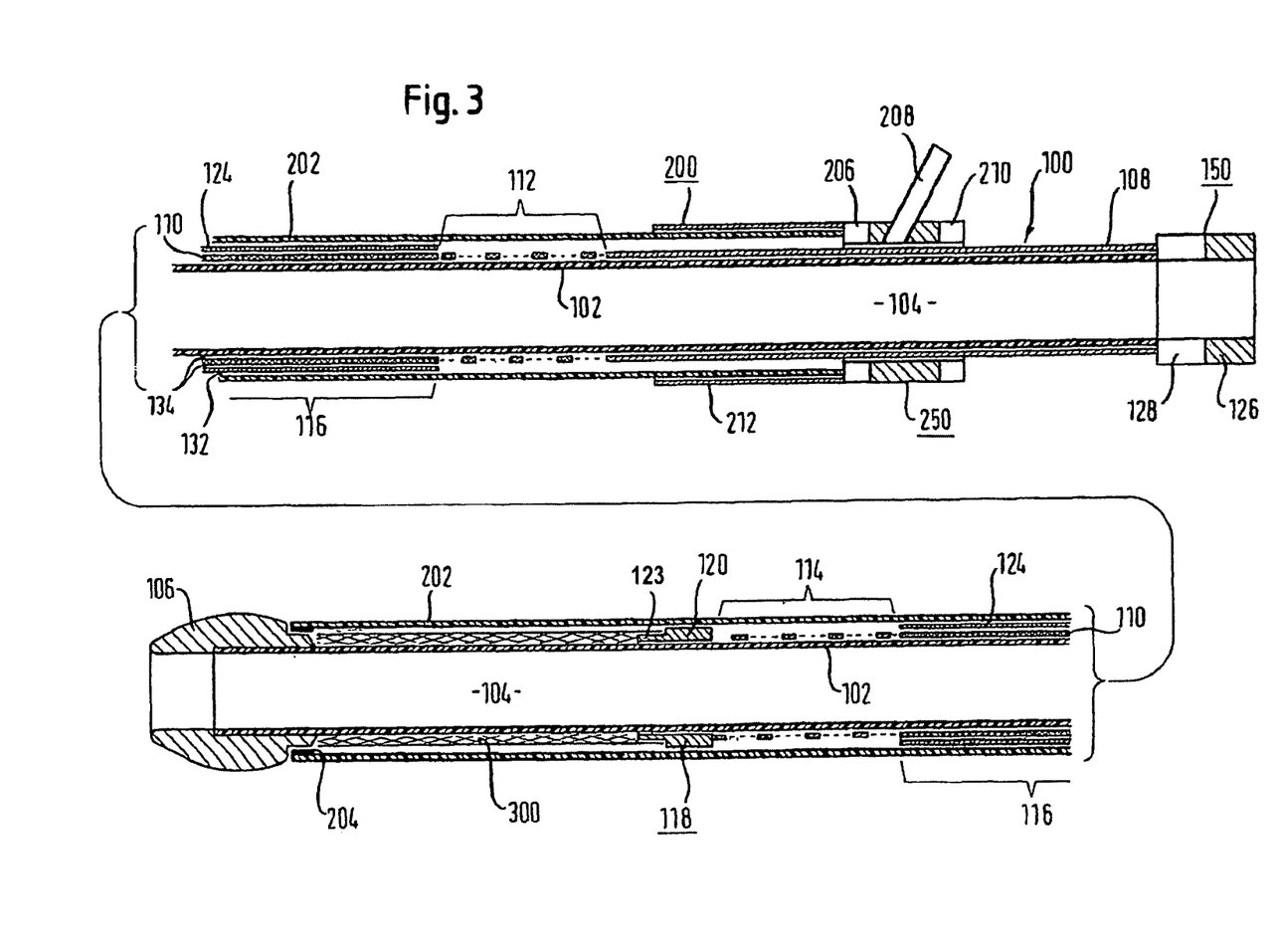
FIG. 3 is a longitudinal diametrical section through one possible embodiment of a medical surgical device.

FIG. 3 shows a medical surgical device for delivering a self-expanding stent. The device comprises a proximal end and a distal end with an elongate, tubular intermediate region. The apparatus comprises an inner catheter 100 and an outer sheath member 200.

The inner catheter comprises an inner tube 102 made from polymeric material having a lumen 104 therethrough which is suitable to be used as a guide wire lumen. At the distal end of the inner tube there is a tip 106, made from Pellethane, glued to the distal end of the inner tube with DYMAX glue. Disposed about the inner tube, at a proximal region of the inner tube, is a rigid, stainless steel push rod 108. A stainless steel wire coil 110 abuts the distal end of the push rod and is disposed around substantially the remaining length of the inner tube, except for a small distal region of the inner tube proximal of the Pellethane tip. The wire coil has a proximal region 112 and a distal region 114 having open-coil structures and an intermediate region 116 having a closed-coil structure. Abutting the distal end of the wire coil and disposed around the inner tube is a pusher element 118 made from PEEK consisting of a proximal flange-like portion 120 and a distal shoulder portion 123. The pusher element is joined to the wire coil (not shown in FIG. 3) as explained above by reference to FIG. 2. The wire coil is joined at the proximal end to the distal end of the push rod, either in like manner or in any other way chosen by a person skilled in designing stent delivery systems. Disposed around the intermediate region of the wire coil is a PTFE shrink-tube 124 constraining the wire coil and preventing the coil from kinking during advancement through a tortuous passageway. This helps to increase the compression resistance of the wire coil, by preventing the adjacent turns of the coil from overlapping, without substantially reducing the flexibility of the wire coil. At the proximal end of the inner catheter 100 is a Luer 126 and a swivel nut 128 connected to a first part 150 of a proximal actuating means. Luer 126 provides access to the guide wire lumen 104.

The outer tubular member comprises a sheath 202 extending from near the proximal end of the inner tubular member to the distal end of the inner tube and abutting the Pellethane tip. The sheath is disposed tightly about the PTFE shrink-tube 124 of the inner catheter 100, leaving substantially no gap between the two, the existing gap being filled by a lubricious material 132, which is a silicone coating on the outer surface of the PTFE shrink-tube. The sheath is slideable in a proximal direction over the inner catheter and is made from the thermoplastic elastomer HYTREL.

At the distal end of the sheath, on an inner surface, there is a radiopaque marker band 204 for determining the location of the distal end of the surgical apparatus during insertion through a body lumen using visualizing means such as radioscopy. The pusher 120 functions as a further radiopaque marker band located at the proximal end of the stent bed. When the sheath is retracted, complete retraction is observable by the radiopaque marker band 204 on the distal end of the sheath 202 aligning with the radiopaque marker band 130 at the distal end of the wire coil 110.

At the proximal end of the outer tubular member there is a second part 250 of the proximal actuating means, also comprising a swivel nut 206 for locking the position of the outer sheath member 200 relative to the inner coil member 100, to prevent unwanted retraction of the sheath during insertion of the medical surgical device. There is a second Luer 208 connected with the second part 250 of the actuating means to provide access to the fluid flow path 134 defined between the inner tube 102, outer tube 124 and adjacent turns of the wire coil 110. Access into the flow path is achieved by fluid passing into the open-coil structure of the wire coil at the proximal end, via the second Luer and then into the gaps between the coils between the inner tube and outer tube. There is further provided a Tuohy Borst valve 210 to prevent fluid escaping proximally from the sheath member. Disposed around a proximal region of the sheath is a rigid, tubular support member 212.

A self-expanding stent 300 is contained within the apparatus at a distal region in the stent bed between the Pellethane tip 106 and PEEK pusher element 118. The proximal end of the self-expanding stent 300 abuts the flange portion 120. This prevents the stent from moving proximally relative to the inner tube 102 during retraction of the sheath 202. The sheath is disposed over the entire length of the self-expanding stent and maintains the stent in a first, radially compressed state. When the sheath is retracted, the stent begins to expand and is held in the correct deployment position by forces from the sheath and pusher element. The operation of the medical surgical apparatus will now be described.

Prior to the insertion into a body lumen, any air within the device is removed by passing flushing fluid from the proximal end to the distal end of the device through the fluid flow path 132 via the second Luer 208, and through the central lumen 104 via the first Luer 126. Swivel nut 206 is tightened to lock the position of the outer sheath member 200 relative to the inner coil member 100. The tip 106 of the medical surgical apparatus is then inserted into a body lumen. It follows a path along a previously inserted guide wire which runs through the inner lumen 104. The apparatus is advanced until the distal end reaches the treatment site.

The position and orientation of the medical surgical apparatus within the body lumen can be visualized using a radioscope to monitor pulses of contrast fluid injected into the body lumen through the internal lumen 134 of the medical surgical device. Radiopaque markers 204 and 120 can then be used to correctly position the stent across the treatment zone.

Once the stent is correctly positioned, the swivel nut 206 is released, and the sheath 202 can be retracted by moving the second part of the actuating means 250 proximally towards the first part of the actuating means 150. As the sheath is retracted, the self-expanding stent 300 is released, and expands to engage and hold apart the inner wall of the body lumen. Once the radiopaque marker bands 204 and 120 have been observed to be aligned, the stent is fully deployed and the medical surgical apparatus can be retracted, the Pellethane tip able to return proximally through the inner lumen of the expanded stent.

The illustrated embodiments are Examples within the scope of the claims that follow. The invention is applicable to a range of implant delivery systems beyond those for self-expanding stents. It is applicable to both over the wire and rapid exchange systems, as well as to systems which lack any guidewire lumen at all. Evidently the skilled reader will bring his/her specialist background knowledge to bear, when extracting useful teaching from the above description.

What is claimed is:

1. A percutaneous, transluminal system with a distal end for inserting into a body and a proximal end to remain outside the body, the system including:
   an inner catheter, comprising:
      an inner tube,
      a wire coil disposed around at least a portion of the inner tube, having a distal region, an intermediate region and a proximal region, and including a closed-coil structure in the intermediate region and an open-coil structure in at least one of the distal region and the proximal region, an outer tube disposed around at least a portion of the wire coil, and a flow path for liquid from the proximal end through the distal end of the system, including a radially-extending portion through the open-coil structure;

an outer sheath disposed around at least a portion of the length of said inner catheter, the outer sheath being retractable in a proximal direction relative to the inner catheter; and a self-expanding stent positioned around the inner tube wherein the self-expanding stent is maintained in a medical-device-receiving annulus inside the outer sheath near the distal end, the self-expanding stent being releasable by the retraction of the outer sheath in a proximal direction relative to the inner catheter;

wherein the self-expanding stent is held within the outer sheath and is positioned distal of the distal end of the wire coil;

the self-expanding stent is maintained in a radially compressed first state by the outer sheath being disposed about at least a portion of the self-expanding stent;

during retraction of the outer sheath, the self-expanding stent is prevented by the wire coil from moving with the outer sheath in a proximal direction; and when the outer sheath is retracted in a proximal direction relative to the inner catheter, the self-expanding stent is released for expansion to a radially less compressed second state.

2. The system of claim 1, wherein the wire coil has an open-coil structure in both the distal region and the proximal region such that the flow path for liquid includes a radially-extending portion through both the distal region and the proximal region.

3. The system of claim 1, wherein the wire coil defines at least a portion of the liquid flow path to be a helical path defined by the adjacent turns of the coil.

4. The system of claim 1, wherein the wire coil defines at least a portion of the liquid flow path to be an annular path bounded by the inner tube and the adjacent turns of the coil.

5. The system of claim 1, wherein the outer tube is a shrink-tube constraining the wire coil.

6. The system of claim 1, wherein the outer tube comprises PTFE.

7. The system of claim 1, wherein the inner tube defines an inner guide-wire lumen.

8. The system of claim 1, further comprising a tip mounted to the inner tube at the distal end thereof.

9. The system of claim 1, wherein the inner tube defines a medical-device-receiving annulus around a distal portion of the inner tube, which is distal of the distal end of the wire coil and the outer tube and proximal of the distal end of the inner tube; the medical-device-receiving annulus providing an exposed portion of the inner tube such that the self-expanding stent may directly contact the inner tube.

10. The system of claim 1, further including a lubricious coating on an outer surface of the outer tube.

11. The system of claim 1, wherein the inner catheter is configured to resist an associated radially inward contraction of the outer sheath arising from proximal relative movement thereof.

12. The system of claim 1, wherein the outer sheath comprises a thermoplastic elastomeric material.

13. The system of claim 1, further comprising an actuating apparatus connected to a proximal end of the inner catheter and the outer sheath, configured to retract the outer sheath in a proximal direction relative to the inner catheter.

14. The system of claim 1, wherein the self-expanding stent is held within the outer sheath in a position distal of the distal end of the outer tube and in direct contact with the inner tube.

* * * * *